(12) United States Patent
Albakri (10) Patent No.: US 10,850,614 B2
(45) Date of Patent: Dec. 1, 2020

(54) BLOOD ALCOHOL LEVEL SENSING SYSTEM FOR A VEHICLE

(71) Applicant: Sadeq Albakri, Brooklyn, NY (US)

(72) Inventor: Sadeq Albakri, Brooklyn, NY (US)

( * ) Notice: Subject to any disclaimer, the term of this patent is extended or adjusted under 35 U.S.C. 154(b) by 127 days.

(21) Appl. No.: 16/271,715

(22) Filed: Feb. 8, 2019

(65) Prior Publication Data

US 2019/0248237 A1    Aug. 15, 2019

Related U.S. Application Data (60) Provisional application No. 62/628,708, filed on Feb. 9, 2018.

(51) Int. Cl.

| | | |
|---|---|---|
| *B60K 28/06* | (2006.01) | |
| *G01N 33/487* | (2006.01) | |
| *G01N 33/49* | (2006.01) | |
| *A61B 5/00* | (2006.01) | |
| *A61B 5/145* | (2006.01) | |
| *A61B 5/1477* | (2006.01) | |
| *A61B 5/1455* | (2006.01) | |
| *A61B 5/024* | (2006.01) | |
| *B62D 1/04* | (2006.01) | |
| *B62D 1/06* | (2006.01) | |
| *B60Q 1/50* | (2006.01) | |

(52) U.S. Cl.
CPC ............ *B60K 28/063* (2013.01); *A61B 5/002* (2013.01); *A61B 5/02433* (2013.01); *A61B 5/1455* (2013.01); *A61B 5/1477* (2013.01); *A61B 5/14546* (2013.01); *A61B 5/4266* (2013.01); *A61B 5/6893* (2013.01); *B62D 1/046* (2013.01); *G01N 33/48714* (2013.01); *G01N 33/48792* (2013.01); *G01N 33/492* (2013.01); *B60Q 1/50* (2013.01); *B62D 1/06* (2013.01)

(58) Field of Classification Search
CPC .... B60K 28/063; B62D 1/046; A61B 5/4845; A61B 5/6893; G01N 33/48714
See application file for complete search history.

(56) References Cited

U.S. PATENT DOCUMENTS

| | | | | |
|---|---|---|---|---|
| 5,743,349 A | * | 4/1998 | Steinberg ............. | B60K 28/063 180/272 |
| 5,793,292 A | * | 8/1998 | Ivey, Jr. ................... | A61B 5/18 340/576 |
| 5,969,615 A | * | 10/1999 | Ivey, Jr. ................... | A61B 5/18 180/272 |

(Continued)

FOREIGN PATENT DOCUMENTS

| | | | | |
|---|---|---|---|---|
| CN | 106274482 A | * | 1/2017 | |
| DE | 102007044692 A1 | * | 5/2008 | ........... B60K 28/063 |
| JP | 2009073422 A | * | 4/2009 | |

*Primary Examiner* — John Villecco
(74) *Attorney, Agent, or Firm* — Bruce A. Lev (57) ABSTRACT

A blood alcohol level sensing system for a vehicle is steering wheel with infrared sensors that are able to detect variations in body chemistry from contact with the palms of the hands to determine if a driver is either alcohol impaired or impaired from certain medical conditions that might affect driving. The system has a digital readout that may be located on the dashboard of the vehicle, and the readout may also be transmitted to a cell phone. In the event of an exceedance of a predetermined set point, an interlock will interrupt the start circuit of the vehicle to prevent it from starting.

14 Claims, 5 Drawing Sheets

(56) References Cited

U.S. PATENT DOCUMENTS

| | | | | |
|---|---|---|---|---|
| 6,620,108 B2* | 9/2003 | Duval | | A61B 5/18 340/573.1 |
| 6,886,653 B1* | 5/2005 | Bellehumeur | | B60K 28/063 180/272 |
| 7,173,536 B2* | 2/2007 | Duval | | A61B 5/14546 250/339.12 |
| 7,299,890 B2* | 11/2007 | Mobley | | B60R 25/252 180/272 |
| 7,377,186 B2* | 5/2008 | Duval | | B62D 1/046 73/23.2 |
| 7,413,047 B2* | 8/2008 | Brown | | B60K 28/063 180/272 |
| 7,671,752 B2* | 3/2010 | Sofer | | B60K 28/066 340/576 |
| 8,089,364 B2* | 1/2012 | Sofer | | B60K 28/066 340/576 |
| 8,256,286 B2* | 9/2012 | Carroll | | A61B 5/14517 73/335.04 |
| 8,479,864 B2* | 7/2013 | White | | B60K 28/063 180/272 |
| 8,581,711 B2* | 11/2013 | Morgan | | B60K 28/06 340/426.11 |
| 8,686,864 B2* | 4/2014 | Hannon | | B60K 28/063 340/576 |
| 8,928,470 B2* | 1/2015 | Morgan | | B60K 28/063 340/426.1 |
| 9,280,145 B2* | 3/2016 | Hannon | | B60K 28/063 |
| 9,326,713 B2* | 5/2016 | Carroll | | A61B 5/14517 |
| 9,549,702 B1* | 1/2017 | Kerness | | A61B 5/18 |
| 9,758,039 B2* | 9/2017 | Hannon | | G05B 11/00 |
| 9,775,565 B1* | 10/2017 | Berg-Neuman | | A61B 5/18 |
| 9,901,294 B2* | 2/2018 | Wahnschafft | | A61B 5/082 |
| 10,207,716 B2* | 2/2019 | Liu | | B60W 40/08 |
| 10,349,892 B2* | 7/2019 | Song | | A61B 5/0205 |
| 2004/0083031 A1* | 4/2004 | Okezie | | A61B 5/145 701/1 |
| 2006/0016278 A1* | 1/2006 | Duval | | B62D 1/046 73/864 |
| 2006/0033628 A1* | 2/2006 | Duval | | A61B 5/082 340/576 |
| 2008/0316037 A1* | 12/2008 | Shoji | | G01N 33/4972 340/576 |
| 2010/0121502 A1* | 5/2010 | Katayama | | B60K 28/063 701/1 |
| 2011/0178382 A1* | 7/2011 | Topp | | B60R 25/00 600/365 |
| 2012/0046571 A1* | 2/2012 | Varpula | | A61B 5/4845 600/547 |
| 2012/0073892 A1* | 3/2012 | Hunter | | B60K 28/063 180/273 |
| 2013/0027209 A1* | 1/2013 | Carroll | | A61B 5/1477 340/576 |
| 2015/0051807 A1* | 2/2015 | Desai | | G01N 33/98 701/99 |
| 2015/0112164 A1* | 4/2015 | Heikenfeld | | A61N 1/325 600/307 |
| 2016/0001781 A1* | 1/2016 | Fung | | B60W 40/08 701/36 |
| 2017/0050519 A1* | 2/2017 | Cristofaro | | B60W 40/08 |
| 2017/0100035 A1* | 4/2017 | Heikenfeld | | A61B 5/0205 |
| 2017/0166235 A1* | 6/2017 | Walker | | B60K 37/06 |
| 2018/0336329 A1* | 11/2018 | Walford | | B60W 50/14 |
| 2020/0101982 A1* | 4/2020 | Bowers | | B60W 40/08 |

* cited by examiner

BLOOD ALCOHOL LEVEL SENSING SYSTEM FOR A VEHICLE

CROSS-REFERENCE TO RELATED APPLICATION

The present application is related to and claims priority from prior provisional application Ser. No. 62/628,708, filed Feb. 9, 2018 which application is incorporated herein by reference.

COPYRIGHT NOTICE

A portion of the disclosure of this patent document contains material which is subject to copyright protection. The copyright owner has no objection to the facsimile reproduction by anyone of the patent document or the patent disclosure, as it appears in the Patent and Trademark Office patent file or records, but otherwise reserves all copyright rights whatsoever. 37 CFR 1.71(d).

BACKGROUND OF THE INVENTION

The following includes information that may be useful in understanding the present invention(s). It is not an admission that any of the information provided herein is prior art, or material, to the presently described or claimed inventions, or that any publication or document that is specifically or implicitly referenced is prior art.

1. Field of the Invention

The present invention relates generally to the field of alcohol detection devices and more specifically relates to a blood alcohol level sensing system for a vehicle.

2. Description of the Related Art

Many consumers enjoy relaxing at the end of a hard day by enjoying a glass of wine, beer or some other type of alcoholic beverage. Consumed in moderation, the occasional alcoholic beverage provides a perfectly healthy and socially acceptable way in which to ease the stresses of the day, while enjoying a flavorful beverage in the process. There are many professional studies that have been done by such organizations as the American Diabetes Association and the Harvard School of Medicine which indicate that moderate consumption of alcohol has some healthy benefits. Findings of these studies prove that moderate drinkers tend to have better health and live longer than those who either abstain or those who drink heavily. Those who consume moderate quantities of alcohol are also less likely to have fewer heart attacks and strokes than those who don't drink at all, or those who drink excessively, and are less likely to suffer high blood pressure, peripheral artery disease, Alzheimer's, and even the common cold.

While there is little dispute that consuming alcohol responsibly is a perfectly safe and acceptable practice, there are those occasions when one has consumed too much alcohol, thus placing themselves and others at risk for injury. Specifically, there are occasions when one may consume "one too many" alcoholic beverages resulting in intoxication. Once a person has crossed this line, it is also very difficult to realize that their ability to drive has also been impaired and they become at risk of either injuring or killing another person by driving anyway, or at risk of being stopped by law enforcement. Either one will change the life of the beverage consumer.

Attempts to solve this problem are systems that can be installed on a vehicle that test the driver's blood alcohol level using a breathalyzer method. The problem that these systems have is that the time required for an analysis can take extra time while the driver waits for the results. This can be a problem when time is not a luxury, such as in an emergency. This method can also be fallible and provide false positive readings when the driver is actually not impaired. Ketone, cigarette fumes, diabetics' breath, hair sprays, mouthwashes, mints, gum, cough drops, and even tobacco have all been known to have the potential to cause false positive breathalyzer readings there is another invention to put a device behind the steering wheel to measure the alcohol through the air, but if the user fails, this device may read the particles of air (carbon dioxide) from the person who is drunk next to the driver and will disable the car which is a major disadvantage of current systems.

While the number of people driving under the influence (DUI) (of alcohol) arrests made each year varies from state to state, there are literally thousands of DUI arrests made daily in the United States. Over 11,773 DUI related deaths were reported in 2015 alone. According to the National Highway Traffic Safety Administration (NHTSA), nearly 40 percent of all vehicle fatalities are alcohol related. A solution that quickly detects and notifies an alcohol impaired driver of his condition, uses BLUETOOTH technology to display and dial a third party, and disables the driver's vehicle when a predetermined maximum alcohol level threshold is exceeded is needed for the driver's safety and the safety of the general public.

Various attempts have been made to solve the above-mentioned problems such as those found in U.S. Pat. No. 6,886,653 to Dennis Bellehumeur; U.S. Pat. No. 7,413,047 to Betty J. Brown et al.; and U.S. Pat. No. 7,911,350 to Rihito Shoji et al. This art is representative of alcohol detection devices. None of the above inventions and patents, taken either singly or in combination, is seen to describe the invention as claimed.

Ideally, alcohol detection devices should provide quick detection and notification to an alcohol impaired driver of his condition, uses BLUETOOTH technology to display the result of a reading, sends a phone notification to a third party, and disables the driver's vehicle when a predetermined maximum alcohol level threshold is exceeded, and yet, would operate reliably and be manufactured at a modest expense. Thus, a need exists for a reliable a blood alcohol level sensing system for a vehicle to avoid the above-mentioned problems.

BRIEF SUMMARY OF THE INVENTION

In view of the foregoing disadvantages inherent in the known alcohol detection devices art, the present invention provides a novel a blood alcohol level sensing system for a vehicle. The general purpose of the present invention, which will be described subsequently in greater detail, is to provide quick detection and notification to an alcohol impaired driver of his condition, uses BLUETOOTH technology to display the result of a reading, provides phone notification to a third party, and disables the driver's vehicle when a predetermined maximum alcohol level is exceeded.

The blood alcohol level sensing system for a vehicle preferably comprises a steering wheel having a circular grip portion with a front side and a back side, and the front side and the back side is integrally formed such that the circular grip portion has a circular cross section. A plurality of blood chemistry sensors are located equidistantly around the front side of the steering wheel and are adapted to detect a blood chemistry from the palms of a user driver upon contact.

The center hub portion of the steering wheel is attached to the steering shaft of the steering column on the vehicle and is adapted to provide a steering means for the vehicle. A blood chemistry processor is adapted to receive a plurality of signals from the plurality of blood chemistry sensors and to transpose the signals into a numerical value and to interrupt the starting circuit of the vehicle when the blood alcohol level of the user driver exceeds a predetermined threshold.

A digital display screen is adapted to receive a numerical value from the blood chemistry processor and to visually display the numerical value to indicate the blood alcohol level of the user driver. A plurality of electric wires are attached to the plurality of blood chemistry sensors, to the blood chemistry processor, and to the digital display screen so that the blood alcohol level of the user driver is able to be determined via the plurality of blood chemistry sensors and the blood chemistry processor, and to output the numerical value to be displayed on the digital display screen so it can be viewed by the driver.

The blood alcohol level sensing system for a vehicle is useful for determining the blood alcohol level of the user driver via the plurality of blood chemistry sensors and the blood chemistry processor and for displaying the blood alcohol level visually on the digital display screen. The blood alcohol level sensing system is also useful for disabling the starting circuit of the vehicle when a predetermined set point that corresponds to a particular blood alcohol level is exceeded, thereby providing a measure of safety for the driver and for the welfare of the public in general. The blood chemistry sensors may be formed as transdermal sensors that may be adapted to deliver pilocarpine to the palms of the driver to thereby cause the palms to perspire in order to reduce the time required for an analysis. The transdermal sensors may be adapted to electrochemically detect the alcohol content of the perspiration from the palms of the user driver.

The blood alcohol level sensing system further may comprise an ignition interlock adapted to interrupt the starting circuit of the vehicle when the blood alcohol level set point is exceeded by the driver. The blood chemistry processor is adapted to include BLUETOOTH technology and is adapted to transmit the blood alcohol level of the user driver to be displayed on at least one display screen of a chosen electronic receiver. The chosen electronic receiver may be a smart phone or may be an LCD screen located on the dash of the vehicle. The electronic receiver may also be a smart phone in the possession of a third party.

The blood chemistry sensors may be formed as infrared body chemistry sensors. The blood chemistry sensors may be adapted to analyze the perspiration using chemicals chosen from the group consisting of: sulfuric acid, potassium dichromate, silver nitrate, and water. The infrared body chemistry sensors may also be adapted to detect an abnormal blood sugar level, to detect heart arrhythmia, or to detect low body oxygen levels. The blood chemistry processor may also be adapted to activate the hazard lights of the vehicle when the predetermined blood alcohol level threshold is exceeded.

The steering wheel is adapted to include a plurality of touch sensors and the touch sensors are activated via the existing seat weight sensor of the vehicle. The touch sensors may be adapted to deliver pilocarpine to the front side of the steering wheel via an activation of the existing seat weight sensor to contact the palms of the driver to cause perspiration that in turn may be analyzed for a variety of impairment factors. The infrared body chemistry sensors may also be adapted to compare minute variations in reflected light against a baseline reading in order to determine impairment.

The present invention holds significant improvements and serves as a blood alcohol level sensing system for a vehicle. For purposes of summarizing the invention, certain aspects, advantages, and novel features of the invention have been described herein. It is to be understood that not necessarily all such advantages may be achieved in accordance with any one particular embodiment of the invention. Thus, the invention may be embodied or carried out in a manner that achieves or optimizes one advantage or group of advantages as taught herein without necessarily achieving other advantages as may be taught or suggested herein. The features of the invention which are believed to be novel are particularly pointed out and distinctly claimed in the concluding portion of the specification. These and other features, aspects, and advantages of the present invention will become better understood with reference to the following drawings and detailed description.

BRIEF DESCRIPTION OF THE DRAWINGS

The figures which accompany the written portion of this specification illustrate embodiments and method(s) of use for the present invention, a blood alcohol level sensing system for a vehicle, constructed and operative according to the teachings of the present invention.

The various embodiments of the present invention will hereinafter be described in conjunction with the appended drawings, wherein like designations denote like elements.

DETAILED DESCRIPTION

As discussed above, embodiments of the present invention relate to a alcohol detection devices and more particularly to a blood alcohol level sensing system for a vehicle as used to improve the detection time and notification to an alcohol impaired driver of his condition, uses BLUETOOTH technology to display the result of a reading, phone dialing to a third party, and disables the driver's vehicle when a predetermined maximum alcohol level is exceeded.

Generally speaking, a blood alcohol level sensing system for a vehicle is steering wheel with infrared sensors that are able to detect variations in body chemistry from contact with the palms of the hands to determine if a driver is either alcohol impaired or impaired from certain medical conditions that might affect driving. The system has a digital readout that may be located on the dashboard of the vehicle, and the readout may also be transmitted to a cell phone. In the event of an exceedence of a predetermined set point, an interlock will interrupt the start circuit of the vehicle to prevent it from starting.

Figure 1:
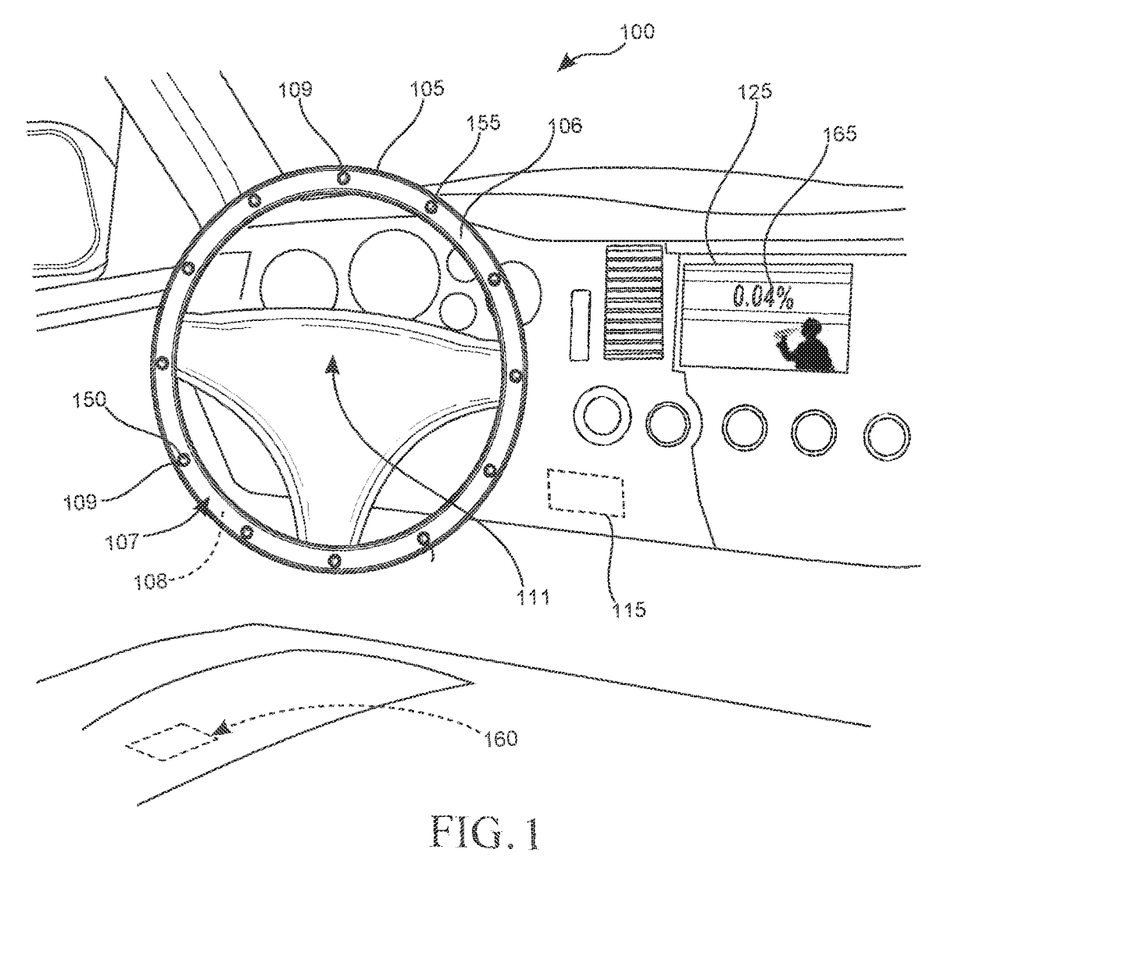
FIG. 1 shows a perspective view illustrating a blood alcohol level sensing system for a vehicle according to an embodiment of the present invention.

Referring to the drawings by numerals of reference there is shown in FIG. 1, a perspective view illustrating blood alcohol level sensing system for a vehicle 100 according to an embodiment of the present invention.

Blood alcohol level sensing system 100 preferably comprises steering wheel 105 having circular grip portion 106 with front side 107 and back side 108, and front side 107 and back side 108 is integrally formed such that circular grip portion 106 has a circular cross section. A plurality of blood chemistry sensors 109 are located equidistantly around front side 107 of steering wheel 105 and are adapted to detect a blood chemistry from the palms of a user driver upon contact.

Figure 2:
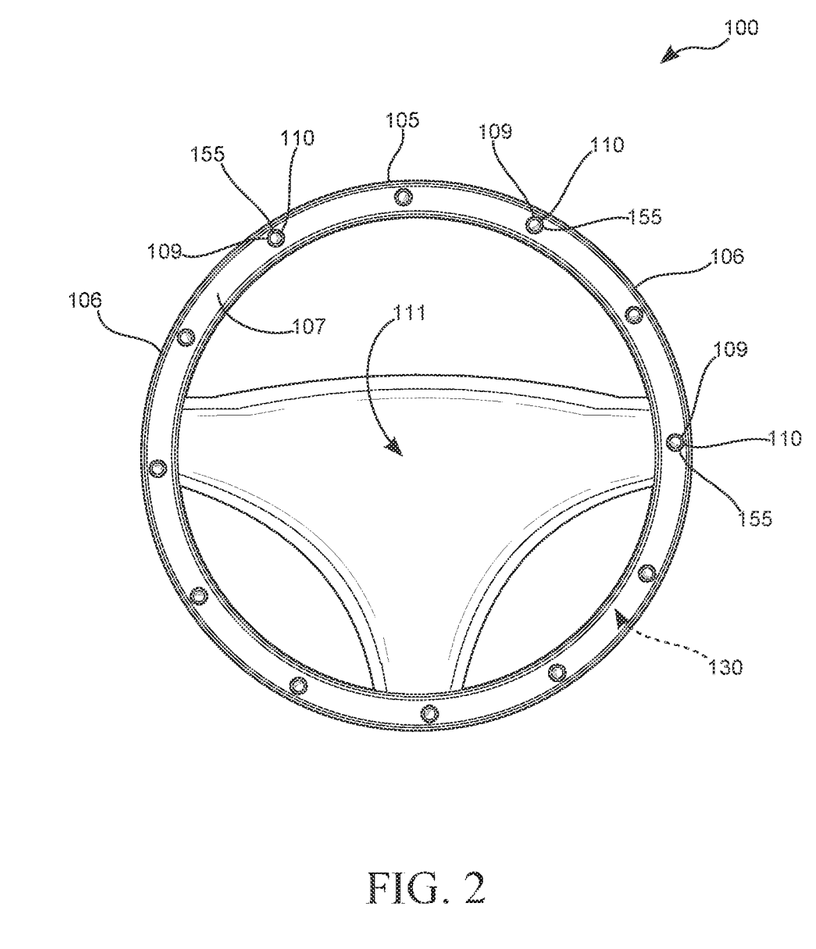
FIG. 2 is a front view illustrating a steering wheel of a blood alcohol level sensing system for a vehicle according to an embodiment of the present invention of FIG. 1.

Referring now to FIG. 2, a front view illustrating steering wheel 105 of blood alcohol level sensing system for a vehicle 100 according to an embodiment of the present invention of FIG. 1.

Blood alcohol level sensing system for a vehicle 100 is useful for determining the blood alcohol level of the user driver via any of blood chemistry sensors 109 and blood chemistry processor 115 and for displaying the blood alcohol level visually on digital display screen 125. Blood alcohol level sensing system 100 is also useful for disabling starting circuit 120 of the vehicle when a predetermined set point that corresponds to a particular blood alcohol level is exceeded, thereby providing a measure of safety for the driver and for the welfare of the public in general. Blood chemistry sensors 109 may be formed as transdermal sensors 110 that may be adapted to deliver pilocarpine to the palms of the user driver to thereby cause the palms to perspire in order to reduce the time required for an analysis. Transdermal sensors 110 may be adapted to electrochemically detect the alcohol content of the perspiration from the palms of the user driver.

Blood alcohol level sensing system 100 further may comprise ignition interlock 135 adapted to interrupt starting circuit 120 of the vehicle when the blood alcohol level set point is exceeded by the driver. Blood chemistry processor 115 is adapted to include BLUETOOTH technology 140 and is adapted to transmit the blood alcohol level of the driver to be displayed on at least one display screen 145 of a chosen electronic receiver 146. The chosen electronic receiver 146 may be smart phone 147 or may be an LCD screen located on the dash of the vehicle. Electronic receiver 146 may also be smart phone 147 in the possession of a third party.

Figure 3:
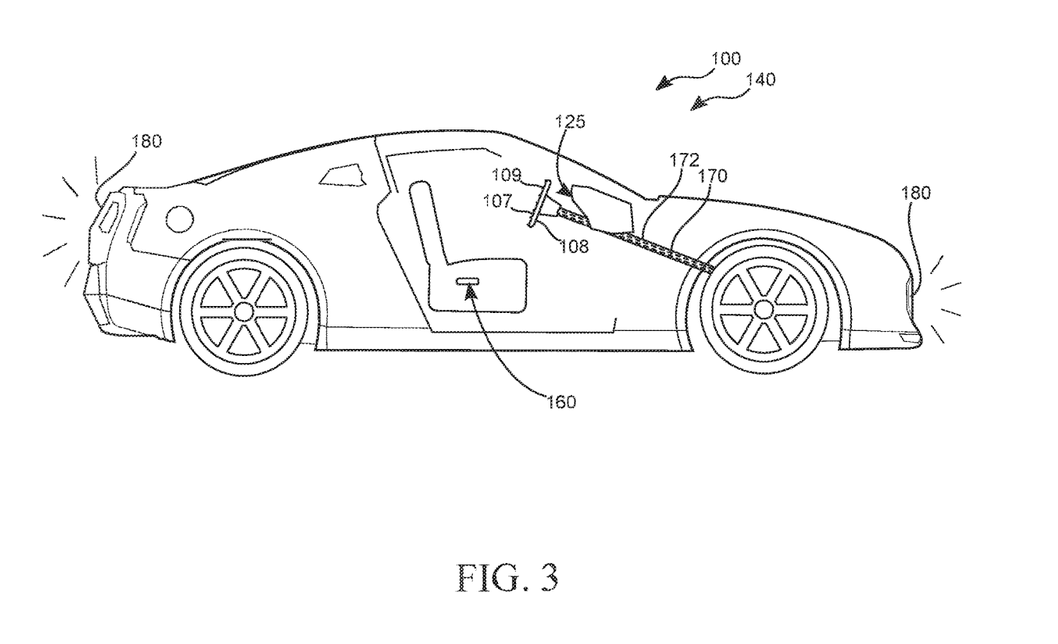
FIG. 3 is a diagram view illustrating a blood alcohol level sensing system for a vehicle according to an embodiment of the present invention of FIG. 1.

Referring now to FIG. 3, is a diagram view illustrating blood alcohol level sensing system for a vehicle 100 according to an embodiment of the present invention of FIG. 1.

Center hub portion 111 of steering wheel 105 is attached to steering shaft 170 of steering column 172 on the vehicle and is adapted to provide a steering means for the vehicle. Blood chemistry processor 115 is adapted to receive a plurality of signals from the plurality of blood chemistry sensors 109 and to transpose the signals into numerical value 165 and to interrupt starting circuit 120 of the vehicle when the blood alcohol level of the user driver exceeds a predetermined threshold. In the event that the driver uses alcohol while driving, blood chemistry sensors 109 will read the elevated alcohol level and when the maximum alcohol level set point is exceeded, the vehicle will begin to flash emergency lights 180 to indicate the vehicle has entered into an emergency mode and begin to slow down until it comes to a gradual stop.

Digital display screen 125 is adapted to receive numerical value 165 from blood chemistry processor 115 and to visually display numerical value 165 to indicate the blood alcohol level of the user driver. A plurality of electric wires 130 are attached to the plurality of blood chemistry sensors 109, to blood chemistry processor 115, and to digital display screen 125 so that the blood alcohol level of the user driver is able to be determined via the plurality of blood chemistry sensors 109 and blood chemistry processor 115, and to output numerical value 165 to be displayed on digital display screen 125 so it can be viewed by the driver.

Figure 4:
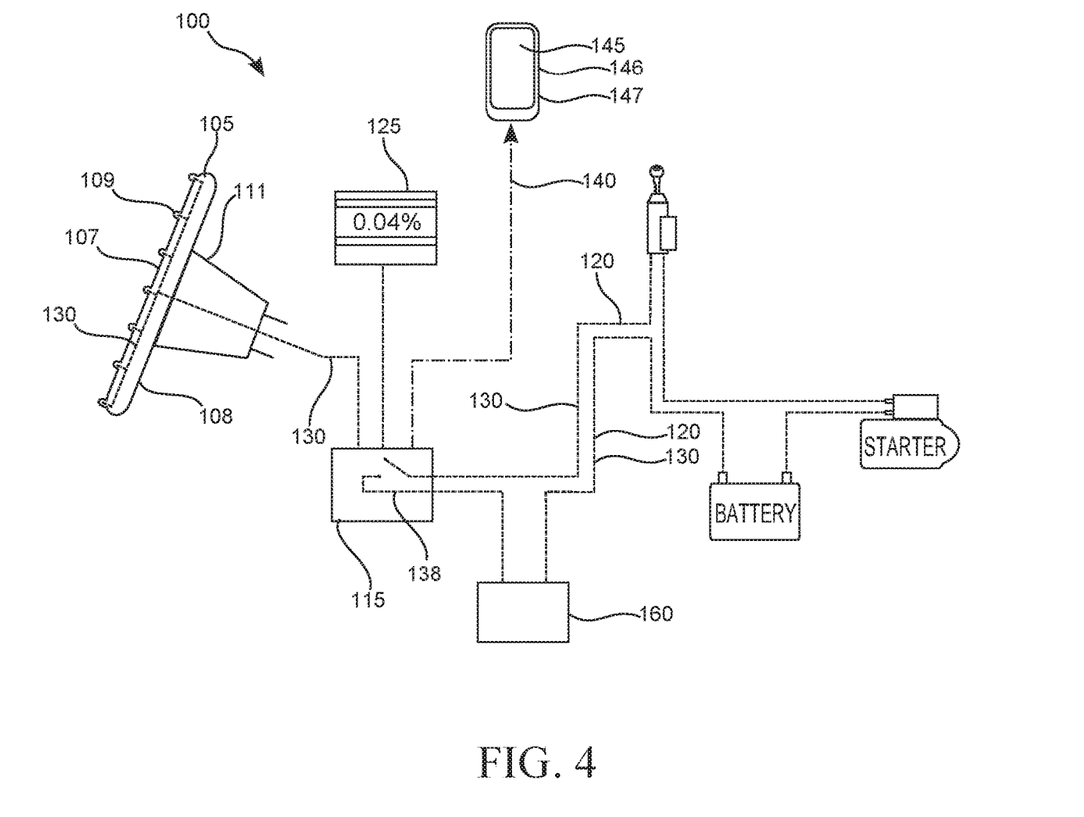
FIG. 4 is a diagram view illustrating a blood alcohol level sensing system for a vehicle according to an embodiment of the present invention of FIG. 1.

Referring now to FIG. 4, is a diagram view illustrating a blood alcohol level sensing system for a vehicle 100 according to an embodiment of the present invention of FIG. 1.

Blood chemistry sensors 109 may be formed as infrared body chemistry sensors 150 and are adapted to compare minute variations in reflected light against a baseline reading in order to determine whether the driver is impaired or not, and to what degree of impairment if the predetermined threshold setting is exceeded. In another embodiment, blood chemistry sensors 109 may be adapted to analyze the perspiration using chemicals chosen from the group consisting of: sulfuric acid, potassium dichromate, silver nitrate, and water. Infrared body chemistry sensors 150 may also be adapted to detect an abnormal blood sugar level, to detect heart arrhythmia, or to detect low body oxygen levels. Blood chemistry processor 115 may also be adapted to activate the hazard lights of the vehicle when the predetermined blood alcohol level threshold is exceeded.

Steering wheel 105 may be adapted to include a plurality of touch sensors 155 in steering wheel 105 that are activated to start operating when the existing driver's seat weight sensor 160 detects a person sitting in the driver's seat of the vehicle. This is so that blood alcohol level sensing system 100 is not operational and using battery power continuously when a driver is not seated in the vehicle. Touch sensors 155 may be adapted to deliver pilocarpine to front side 107 of steering wheel 105 via an activation of the existing seat weight sensor 160, to contact the palms of the driver to cause perspiration that in turn may be analyzed for a variety of impairment factors.

The blood alcohol level sensing system for a vehicle 100 may be manufactured and provided for sale in a wide variety of sizes and shapes for a wide assortment of applications. Upon reading this specification, it should be appreciated that, under appropriate circumstances, considering such issues as design preference, user preferences, marketing preferences, cost, structural requirements, available materials, technological advances, etc., other kit contents or arrangements such as, for example, including more or less components, customized parts, different color combinations, parts may be sold separately, etc., may be sufficient.

Figure 5:
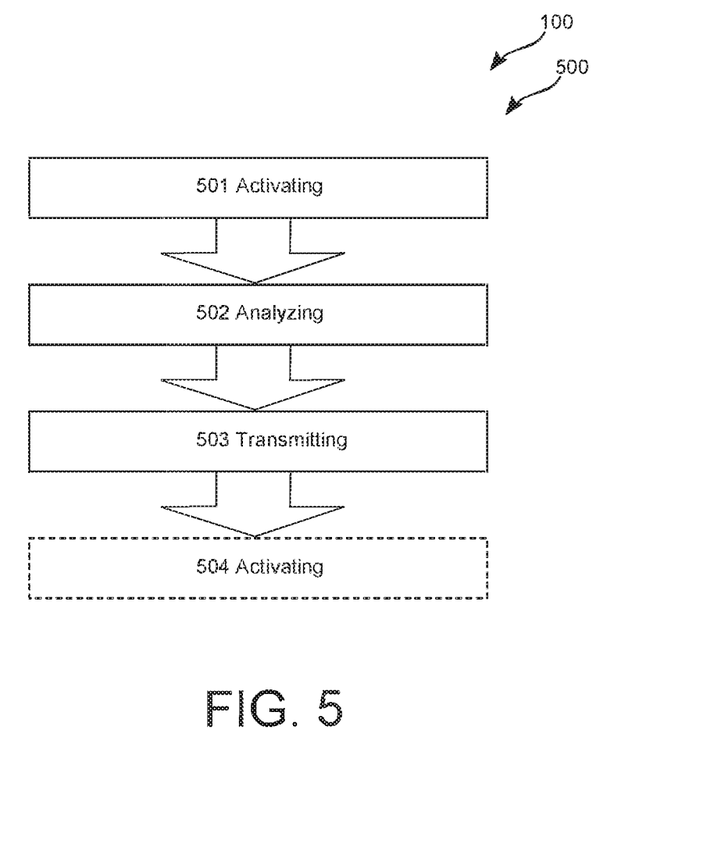
FIG. 5 is a flowchart illustrating a method of use for a blood alcohol level sensing system for a vehicle according to an embodiment of the present invention of FIGS. 1-4.

Referring now to FIG. 5, is a flowchart illustrating method of use 500 for blood alcohol level sensing system for a vehicle 100 according to an embodiment of the present invention of FIGS. 1-4. A method 500 of using blood alcohol level sensing system 100 may comprise the steps of; step one 501 activating at least one touch sensor 155 of steering wheel 105 via existing seat weight sensor 160 of a vehicle; step two 502 analyzing the perspiration from the hand palm of a user to find the blood alcohol percentage; step three 503 transmitting numerical value 165 representing the blood alcohol percentage to be displayed on digital display screen 125; step four 504 activating ignition interlock 135 of a vehicle when a predetermined maximum set point is exceeded.

It should be noted that step 504 is an optional step and may not be implemented in all cases. Optional steps of method 500 are illustrated using dotted lines in FIG. 5 so as to distinguish them from the other steps of method 500.

It should be noted that the steps described in the method of use can be carried out in many different orders according to user preference. The use of "step of" should not be interpreted as "step for", in the claims herein and is not intended to invoke the provisions of 35 U.S.C. § 112, ¶6. Upon reading this specification, it should be appreciated that, under appropriate circumstances, considering such issues as design preference, user preferences, marketing preferences, cost, structural requirements, available materials, technological advances, etc., other methods of use arrangements such as, for example, different orders within above-mentioned list, elimination or addition of certain steps, including or excluding certain maintenance steps, etc., may be sufficient.

The embodiments of the invention described herein are exemplary and numerous modifications, variations and rearrangements can be readily envisioned to achieve substantially equivalent results, all of which are intended to be embraced within the spirit and scope of the invention. Further, the purpose of the foregoing abstract is to enable the U.S. Patent and Trademark Office and the public generally, and especially the scientist, engineers and practitioners in the art who are not familiar with patent or legal terms or phraseology, to determine quickly from a cursory inspection the nature and essence of the technical disclosure of the application.

What is claimed is new and desired to be protected by Letters Patent is set forth in the appended claims:

1. A blood alcohol level sensing system for a vehicle comprising:
    a steering wheel including;
        a circular grip portion having a front side and a back side; and
        a plurality of blood chemistry sensors;
            wherein said front side and said back side of said circular grip portion of said steering wheel are integrally formed such that said circular grip portion has a circular cross section; and
            wherein said plurality of blood chemistry sensors are located equidistantly around said front side of said steering wheel and adapted to detect a blood chemistry from each palm of a user driver upon contact;
    a plurality of touch sensors;
        wherein said plurality of touch sensors are activated via an existing seat weight sensor of said vehicle and wherein said plurality of touch sensors are adapted to deliver pilocarpine to said front side of said steering wheel via an activation of said seat weight sensor;
    a center hub portion;
        wherein said hub portion is attached to a steering shaft of a steering column of said vehicle and is adapted to provide a steering means for said vehicle;
    a blood chemistry processor;
        wherein said blood chemistry processor is adapted to receive a plurality of signals from said plurality of blood chemistry sensors and to transpose said plurality of signals into a numerical value; and
        wherein said blood chemistry processor is adapted to interrupt a starting circuit of said vehicle when said blood alcohol level of said user driver exceeds a predetermined threshold;
    a digital display screen;
        wherein said digital display screen is adapted to receive said numerical value from said blood chemistry processor and to visually display said numerical value to indicate said blood alcohol level of said user driver;
    a plurality of electric wires;
        wherein said plurality of electric wires are attached to said plurality of blood chemistry sensors, to said blood chemistry processor, and to said digital display screen such that said blood alcohol level of said user driver is able to be determined via said plurality of blood chemistry sensors and said blood chemistry processor and to output said numerical value to be displayed on said digital display screen;
    wherein said blood alcohol level sensing system for a vehicle is useful for determining said blood alcohol level of said user driver via said plurality of blood chemistry sensors and said blood chemistry processor and for displaying said blood alcohol level visually on said digital display screen; and wherein said blood alcohol level sensing system for a vehicle is useful for disabling said starting circuit of said vehicle when said predetermined set point corresponding to said blood alcohol level is exceeded thereby providing safety for said user driver and for a general public welfare.

2. The blood alcohol level sensing system of claim 1 wherein said plurality of blood chemistry sensors are transdermal sensors.

3. The blood alcohol level sensing system of claim 2 wherein said transdermal sensors are adapted to electrochemically detect an alcohol content from said perspiration of said palms of said user driver.

4. The blood alcohol level sensing system of claim 1 further comprises an ignition interlock.

5. The blood alcohol level sensing system of claim 4 wherein said ignition interlock is adapted to interrupt said starting circuit of said vehicle.

6. The blood alcohol level sensing system of claim 1 wherein said blood chemistry processor is adapted to include Bluetooth technology.

7. The blood alcohol level sensing system of claim 1 wherein said blood chemistry processor is adapted to transmit said blood alcohol level of said user driver to be displayed on at least one display screen of at least one chosen electronic receiver.

8. The blood alcohol level sensing system of claim 7 wherein said chosen electronic receiver is a smart phone.

9. The blood alcohol level sensing system of claim 1 wherein said plurality of blood chemistry sensors are a plurality of infrared body chemistry sensors.

10. The blood alcohol level sensing system of claim 9 wherein said plurality of infrared body chemistry sensors are adapted to detect an abnormal blood sugar level of said user driver.

11. The blood alcohol level sensing system of claim 9 wherein said plurality of infrared body chemistry sensors are adapted to detect heart arrhythmia.

12. The blood alcohol level sensing system of claim 9 wherein said plurality of infrared body chemistry sensors are adapted to detect low body oxygen levels.

13. The blood alcohol level sensing system of claim 1 wherein said plurality of blood chemistry sensors are adapted to analyze said perspiration using chemicals chosen from the group consisting of sulfuric acid, potassium dichromate, silver nitrate, and water.

14. The blood alcohol level sensing system of claim 1 wherein said blood chemistry processor is adapted to activate a plurality of hazard lights of said vehicle when said predetermined threshold is exceeded.

\* \* \* \* \*